(12) United States Patent
Bäckström et al.

(10) Patent No.: US 6,340,764 B1
(45) Date of Patent: Jan. 22, 2002

(54) REFERENCE COMPOUND FOR USE IN THE ANALYSIS OF LEVOSIMENDAN BATCHES

(75) Inventors: Reijo Bäckström, Helsinki; Tuula Heinonen, Espoo; Tuula Hauta-Aho, Vantaa, all of (FI)

(73) Assignee: Orion Corporation, Espoo (FI)

( * ) Notice: Subject to any disclaimer, the term of this patent is extended or adjusted under 35 U.S.C. 154(b) by 0 days.

(21) Appl. No.: 09/719,806

(22) PCT Filed: Jun. 18, 1999

(86) PCT No.: PCT/FI99/00539

§ 371 Date: Feb. 20, 2001

§ 102(e) Date: Feb. 20, 2001

(87) PCT Pub. No.: WO99/65888

PCT Pub. Date: Dec. 23, 1999

(30) Foreign Application Priority Data

Jun. 18, 1998 (FI) ................................. 981428

(51) Int. Cl.⁷ ...................... C07D 307/32; G01N 30/04; C07C 247/00
(52) U.S. Cl. ........................ 549/321; 514/473; 552/1; 436/98; 436/93
(58) Field of Search ............................ 549/321; 514/473

(56) References Cited

U.S. PATENT DOCUMENTS

6,183,771 B1 * 2/2001 Urtti et al. ................ 424/449

FOREIGN PATENT DOCUMENTS

| EP | 0 359 439 | | 3/1990 |
| EP | 0 383 449 | | 8/1990 |
| GB | 383449 B1 | * | 8/1990 |
| GB | 383449 A2 | * | 8/1990 |
| GB | 0565546 B1 | * | 10/1993 |
| WO | WO 97/35841 | | 10/1997 |
| WO | WO-97/35841 | * | 10/1997 |
| WO | WO-01/00211 A1 | * | 1/2001 |

* cited by examiner

*Primary Examiner*—Floyd D. Higel
*Assistant Examiner*—Kamal Saeed
(74) *Attorney, Agent, or Firm*—Finnegan, Henderson, Farabow, Garrett & Dunner, L.L.P.

(57) ABSTRACT

A pyridazinyl derivative (I) and its use as a reference compound in the determination of potentially genotoxic impurities in levosimendan samples. An analytic method for the determination of potentially genotoxic impurities in levosimendan samples wherein (I) is used as a reference compound. Levosimendan is a medicament useful in the treatment of heart failure.

12 Claims, 2 Drawing Sheets

REFERENCE COMPOUND FOR USE IN THE ANALYSIS OF LEVOSIMENDAN BATCHES

This application is a national stage filing of PCT International Application No. PCT/FI99/00539, filed on Jun. 18, 1999, which published in the English language.

BACKGROUND OF THE INVENTION

The present invention relates to [[4-(2-azido-3-methyl-5-oxotetrahydrofuran-2-yl)phenyl]hydrazono]propanedinitrile (I) and its use as a reference compound in the analysis of batches of levosimendan synthesis, particularly in the determination of potentially genotoxic impurities in samples of a levosimendan batch. The present invention also relates to an analytic method for the determination of potentially genotoxic impurities in samples of a levosimendan batch wherein [[4-(2-azido-3-methyl-5-oxotetrahydrofuran-2-yl)phenyl]hydrazono]propanedinitrile (I) is used as a reference compound.

Levosimendan, which is the (−)-enantiomer of [[4-(1,4,5,6-tetrahydro-4-methyl-6-oxo-3-pyridazinyl)phenyl]hydrazono]propanedinitrile, and the method for its preparation is described e.g. in EP 565546 B1. Levosimendan is potent in the treatment of heart failure and has significant calcium dependent binding to troponin. The use of levosimendan in the treatment of myocardial ischemia is described in WO 93/21921. The hemodynamic effects of levosimendan in man are described in Sundberg, S. et al., Am. J. Cardiol., 1995; 75: 1061–1066. Levosimendan is represented by the formula:

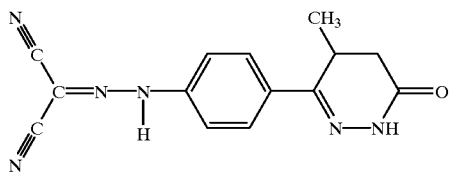

Clinical studies have confirmed the beneficial effects of levosimendan in heart failure patients.

Levosimendan can be prepared in high purity and in nearly quantitative yields by treating (−)-6-(4-aminophenyl)-5-methyl-4,5dihydro-3(2H)pyridazinone with sodium nitrite and malononitrile as described in EP 565546 B1. However, it has been found that samples of levosimendan as synthesized show potential genotoxic properties occasionally in the bacterial mutagenity,test (Ames test).

SUMMARY OF THE INVENTION

It has now been found that the potential genotoxic properties of levosimendan samples are caused by an azido derivative impurity of formula (I)

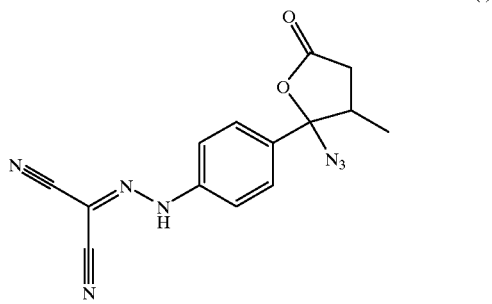

This azido derivative is a potent mutagen which can be formed during levosimendan synthesis in an amount sufficient to give a positive result in the bacterial mutagenity test. This compound named [[4-(2-azido-3-methyl-5-oxotetrahydrofuran-2-yl)phenyl]hydrazono]propanedinitrile (I) is therefore useful as a reference compound in the routine analysis of batches of levosimendan synthesis, particularly in the determination of potentially genotoxic impurities in levosimendan batches. The presence of (I) in a levosimendan batch indicates that further recrystallization is necessary for obtaining levosimendan material suitable for use as a medicine.

DETAILED DESCRIPTION OF THE INVENTION

Figure 1:
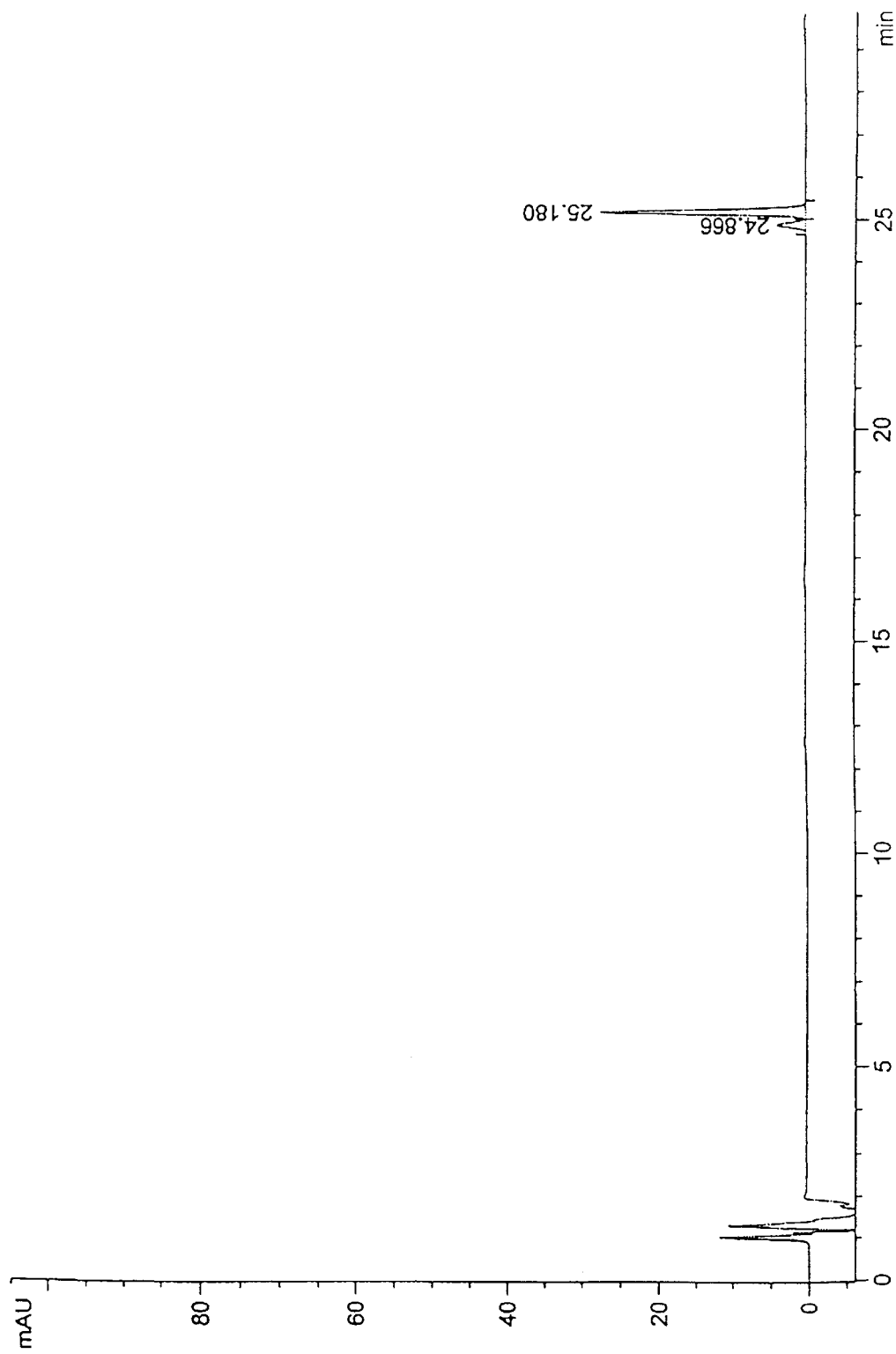
FIG. 1 is a HPLC-chromatogram of the [[4-(2-azido-3-methyl-5-oxotetrahydrofuran-2-yl)phenyl]hydrazono] propanedinitrile standard (0.4 µg/ml).

The present invention provides a reference compound having structure (I) for the determination of potentially genotoxic impurities in samples of a levosimendan batch. The present invention also provides a reference preparation for the determination of potentially genotoxic impurities in samples of a levosimendan batch comprising compound (I) optionally together with an analytically acceptable carrier, and in particular essentially in the absence of pyridazinyl derivatives.

The present invention also provides the use of (I) as a reference compound in the determination of potentially genotoxic impurities in samples of a levosimendan batch.

The present invention also provides an analytic method for the determination of potentially genotoxic impurities in samples of a levosimendan batch characterized in that compound (I) is used as a reference compound, particularly as said levosimendan sample is analyzed by High Pressure Liquid Chromatography (HPLC).

Furthermore, the present invention provides an analytic method for the determination of potentially genotoxic impurities in samples of a levosimendan batch which method comprises preparing a reference standard solution by dissolving compound (I) in solution, preparing a test solution by dissolving a sample of a levosimendan batch in solution, obtaining a HPLC chromatogram of said reference standard solution, obtaining a HPLC chromatogram of said test solution and determining the concentration of compound (I) in the sample.

The term "analytically acceptable carrier" means here a carrier which does not hamper the qualitative or quantitative analysis of (I). The selection of a suitable analytically acceptable carrier is well known to one skilled in the art. An example of an analytically acceptable carrier is dimethyl sulphoxide.

Compound (I) can be prepared by treating 6-(4-aminophenyl)-5-methyl4,5-dihydro-3(2H)-pyridazinone with sodium nitrite and malononitrile wherein sodium nitrite is used in molar excess and separating (I) from the reaction mixture. The procedure is described in detail in Example 1.

The product of a levosimendan batch is preferably analyzed using High Pressure Liquid Chromatography (HPLC). Suitable apparatus include e.g. C-8 reversed phase HPLC column with UV-detection at 360 nm. The mobile phase is e.g. a mixture of phosphate buffer pH 2.1 and acetonitrile. The levosimendan sample is dissolved in suitable solvent such as a mixture of dimethyl sulfoxide, methanol and water. The reference solutions are prepared by dissolving compound (I) in suitable solvent. The retention times of levosimendan and compound (I) or diastereomers thereof are determined in the chromatographic conditions used. The amount of (I) in the levosimendan sample is determined by comparing the chromatograms obtained for the sample solution and the reference solution. The procedure is described in detail in Example 2.

The amount of the undesired impurity (I) in a levosimendan batch can be reduced by methods known in the art such as recrystallization. Recrystallization of levosimendan can be performed from any suitable solvent acetone being the preferred solvent.

EXAMPLES

Example 1

Preparation of [[4-(2-azido-3-methyl-5-oxotetrahydro-furan-2-yl)phenyl]hydrazono]propanedinitrile (mixture of diastereomers)

6-(4-Aminophenyl)-4.5-dihydro-5-methyl-3(2H)pyridazinone (153 g, 0.75 mol) was dissolved in acetic acid (750 mL). Solid sodium nitrite (210 g, 3.0 mol) was slowly added to the solution at 10–20° C. After the addition the mixture was stirred for 90 min at 10–20° C. The reaction mixture was poured rapidly to a 20° C. solution of malononitrile (150 g, 2.3 mol) and water (1500 mL). The resulting mixture was stirred at 20–25° C. for 60 min and then filtered and washed with water. The wet solid was extracted successively with tetrehydrofuran (300 mL) and ethyl acetate (1900 mL). The combined extracts were dried with sodium sulphate and the solvents evaporated under vacuum. The residue was triturated with ethyl acetate (200 mL), filtered and the filtrate was evaporated under vacuum. The residue (8.0 g) was purified chromatographically on silica gel using toluene-ethyl acetate 2:1 as the eluent. After crystallization from toluene the yield of pure mixture of diastereomers was 1.0 g. The major component of the mixture can be enriched by multiple crystallizations from toluene, but for analytical purposes the mixture is adequate. 1H-NMR (400 MHz, DMSO-$d_6$, σ) major diastereomer 1.06 (d,3H, J=6 Hz), 2.55 (dd, 1H, J=16 Hz, 11 Hz), 2.57 (m, 1H), 2.78 (dd, 1H, J=16 Hz, 8 Hz), 7.59 (d. 1H, J=9 Hz), 7.62 (d, 1H, J=9 Hz), 12.6 (broad s, 1H), minor diastereomer 0.60 (d, 3H, J=7 Hz), 2.43 (dd, 1H, J=18 Hz, 2 Hz), 2.78 (m, 1H), 3.14 (dd, 1H, J=8 Hz, 18 Hz), 7.54 (d, 1H, J=9 Hz), 7.61 (d, 1H, J=9 Hz), 12.6 (broad s, 1H).

Example 2

Use of [[4-(2-azido-3-methyl-5-oxotetrahydro-furan-2-yl)phenyl]hydrazono]propanedinitrile (I) as a reference compound in HPLC-chromatography.

The HPLC (High Pressure Liquid Chromatography) method for analysis of compound (I) in levosimendan raw material was based on the C-8 reversed phase HPLC column with UV-detection at 360 nm. The mobile phase consisted of acetonitrile and phosphate buffer pH 2.1.

Reagents:
1. Methanol, HPLC grade
2. Sodium dihydrogen phosphate, $NaH_2PO_4 \times H_2O$, Merck
3. Ortho phosphoric acid, $H_3PO_4$, Merck
4. Phosphate buffer pH 2.1:
   Dissolve 1.8 g of sodium dihydrogen phosphate ($NaH_2PO_4$) in water and add 2.0 ml of phosphoric acid. Adjust the pH if necessary with 2 M sodium hydroxide or 1 M phosphoric acid. Dilute to 1000.0 ml with water.
5. Dimethyl sulphoxide, BDH
6. Acetonitrile, HPLC grade
7. Solvent: Mix 200 ml of methanol with 800 ml of water
8. [[4-(2-azido-3-methyl-5-oxotetrahydro-furan-2-yl) phenyl]hydrazono]-propanedinitrile reference standard Standard solutions (reference preparations of compound (I)):

Stock solution: 10.00 mg of [[4-(2-azido-3-methyl-5-oxotetrahydro-furan-2-yl)phenyl]hydrazono] propanedinitrile is dissolved in a 100 ml volumetric flask in 20 ml of dimethyl sulphoxide and filled to volume with methanol.

Standard solution 1 (50 μg/ml): 5.00 ml of the stock solution is diluted to 10.0 ml with solvent.

Standard solution 2 (0.4 μg/ml=40 ppm): 1.00 ml of the stock solution is diluted to 250.0 ml with solvent.

Quantitation limit solution (0.1 μg/ml=10 ppm): 5.00 ml of standard solution 2 is diluted to 20.0 ml solvent.

Test solution 100 mg of test sample is dissolved in a 10 ml volumetric flask in 8 ml of dimethyl sulphoxide and filled to volume with solvent.

Chromatographic conditions:

| Apparatus | Liquid chromatograph |
|---|---|
| Detector | UV-VIS, detection wavelength 360 nm |
| Column | Symmetry C 8, 3.0 μm, 7.5 cm × 4.6 mm |
| Oven temperature | ambient |
| Mobile phase | A: phosphate buffer pH 2.1 |
| | B: acetonitrile |
| % B | 0 min 20% |
| | 5 min 30% |
| | 15 min 30% |
| | 30 min 90% |
| Flow rate | 0.8 ml/min |
| Injection volume | 100 μl |
| Run time | 30 min |
| Post time | 10 min |
| Retention times: | levosimendan about 13 min |
| | Compound (I) minor diastereomer: about 24 min |
| | Compound (I) major diastereomer: about 25 min |

System suitability
1. Replicate injections of quantitation limit solutions must be repeatable;
   6 injections, RSD=10.0%.

Procedure

After the system suitability criteria are met, proceed with the standard and sample injections.

Calculations

The concentration of the major diastereomer of compound (I) in ppm will be calculated according to the following equation:

$$\frac{C_{st} \cdot R_x \cdot 10 \cdot 1000000}{R_{st} \cdot w}$$

$C_{st}$=concentration of the major diastereomer of compound (I) in [[4-(2-azido-3-methyl-5-oxotetrahydro-furan-2-yl)phenyl]hydrazono]propane-dinitrile standard solution (mg/ml)

$R_x$=the peak area of the major diastereomer of compound (I) in the chromatogram of the test solution $R_{st}$=the peak area of the major diastereomer of compound (I) in the chromatogram of the [[4-(2-azido-3-methyl-5-oxotetrahydro-furan-2-yl)-phenyl]hydrazono] propanedinitrile standard solution w=weight of the sample 10=dilution factor of the sample (ml)

The concentration of the minor diastereomer of compound (I) in ppm will be calculated according to the following equation. The major diastereomer of compound (I) is used as a reference standard.

$$\frac{C_{st} \cdot R_x \cdot 10 \cdot 1000000}{R_{st} \cdot w} \cdot 1.023$$

$C_{st}$=concentration of the minor diastereomer of compound (I) in [[4-(2-azido-3-methyl-5-oxotetrahydro-furan-2-yl)phenyl]hydrazono]propane-dinitrile standard solution (mg/ml)

$R_x$=the peak area of the minor diastereomer of compound (I) in the chromatogram of the test solution $R_{st}$=the peak area of the minor diastereomer of compound (I) in the chromatogram of the [[4-(2-azido-3-methyl-5-oxotetrahydro-furan-2-yl)-phenyl]hydrazono] propanedinitiile standard solution w=weight of the sample 10=dilution factor of the sample (ml)

1.023=correction factor for the minor diastereomer of compound (I)

Figure 2:
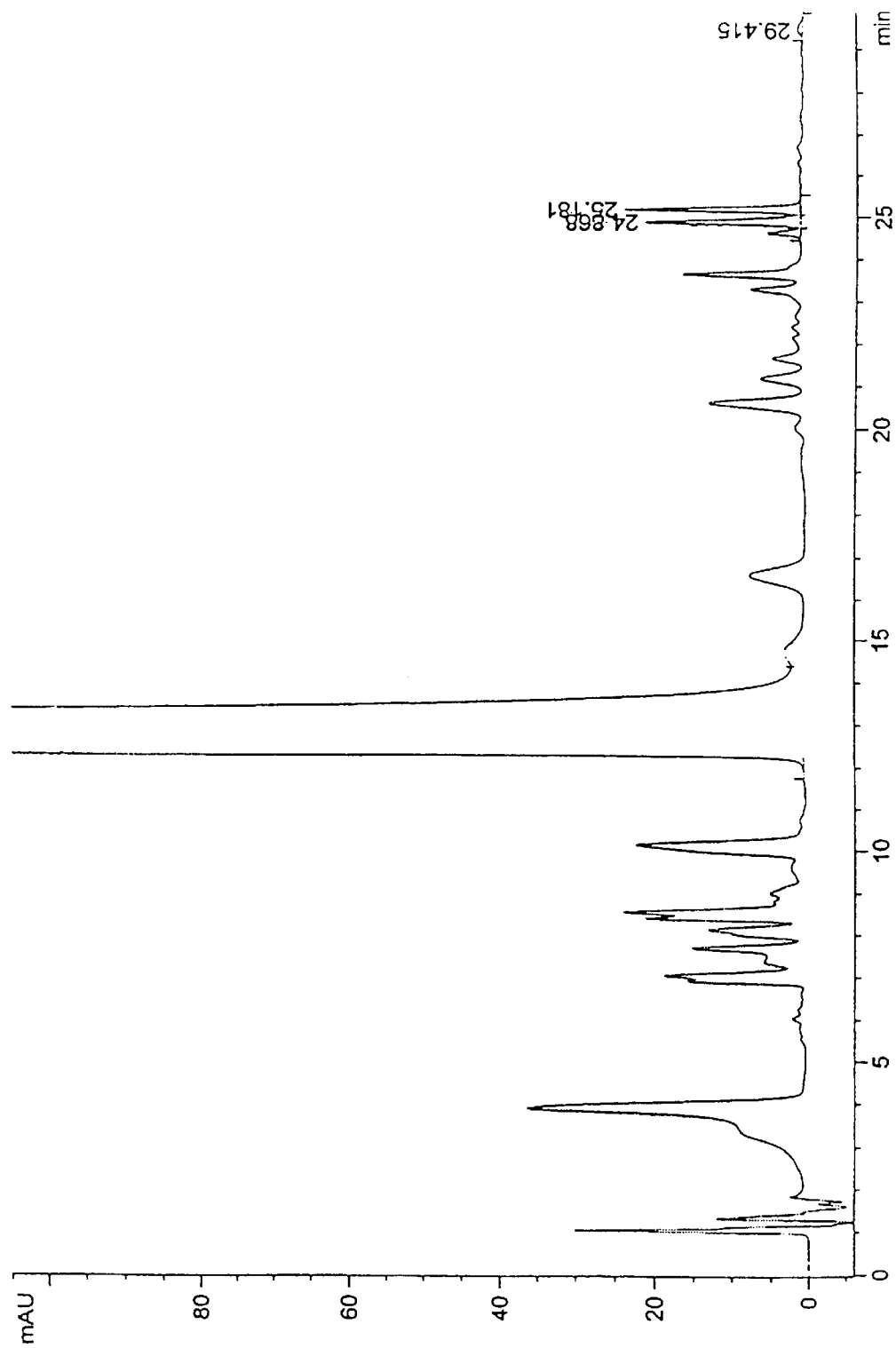
FIG. 2 is a HPLC-chromatogram of levosimendan raw material.

The chromatogram of the [[4-(2-azido-3-methyl-5-oxotetrahydro-furan-2-yl)phenyl]hydrazono] propanedinitrile standard (0.4 µg/ml) obtained is shown in FIG. 1. The retention time for the major diastereomer of compound (I) is 25.180 min and for the minor diastereomer of compound (I) 24.866 min. The chromatogram of levosimendan raw material is shown in FIG. 2.

What is claimed is:

1. A compound of formula I

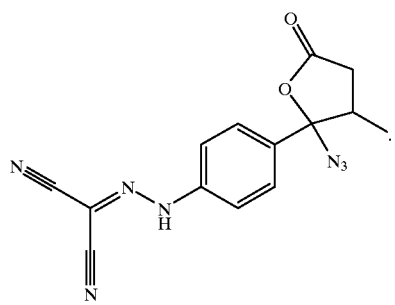

(I)

2. A composition for the determination of potentially genotoxic impurities in a sample of levosimendan, which comprises a compound of claim 1.

3. A composition according to claim 2, containing no pyridazinyl compounds.

4. A composition for the determination of potentially genotoxic impurities in a sample of levosimendan, which comprises a compound of claim 1 together with an analytically acceptable carrier.

5. A composition according to claim 4, containing no pyridazinyl compounds.

6. An analytic method for the determination of potentially genotoxic impurities in a sample of levosimendan, which method comprises preparing a reference standard solution by dissolving a compound of claim 1 in solution, preparing a test solution by dissolving the sample of levosimendan in solution, obtaining a HPCL chromatogram of said reference standard solution, obtaining a HPLC chromatogram of said test solution and determining the concentration of compound of claim 1 in the sample.

7. An analytic method for the determination of potentially genotoxic impurities in a sample of levosimendan, which comprises comparing an analysis of composition as claimed in claim 2 to an analysis of the sample of levosimendan.

8. A method according to claim 7, wherein the analysis of the composition and the analysis of the sample of levosimendan is an HPLC analysis.

9. An HPLC chromatogram of composition as claimed in claim 2.

10. A method of determining the concentration of a compound of formula I in a sample of levosimendan,

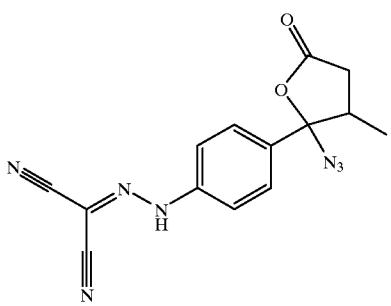

(I)

which comprises comparing an analysis of a reference preparation as claimed in claim 2 to an analysis of the sample of levosimendan.

11. A method according to claim 10, wherein the analysis of the composition and the analysis of the sample of levosimendan is an HPLC analysis.

12. A mixture of compounds of formula I according to claim 1, wherein the compounds are of one diastereomer or a mixture of diastereomers.

* * * * *